United States Patent
Blickhan et al.

(10) Patent No.: US 6,358,420 B2
(45) Date of Patent: *Mar. 19, 2002

(54) BLOOD COLLECTION METHOD EMPLOYING AN AIR VENTING BLOOD SAMPLE TUBE

(75) Inventors: Bryan J Blickhan, Zion; Daniel Lynn, Spring Grove, both of IL (US)

(73) Assignee: Baxter International Inc., Deerfield, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/088,231

(22) Filed: Jun. 1, 1998

(51) Int. Cl.⁷ .............................................. B01D 37/00
(52) U.S. Cl. ...................... 210/663; 210/767; 210/782
(58) Field of Search ................................. 210/669, 767, 210/782, 120, 136, 257.1, 436, 472, 660, 663

(56) References Cited

U.S. PATENT DOCUMENTS

| | | | |
|---|---|---|---|
| 3,058,799 A | 10/1962 | Rowles, Jr. .................. | 422/26 |
| 5,128,048 A | 7/1992 | Stewart et al. ............... | 210/749 |
| 5,167,656 A | 12/1992 | Lynn ........................... | 604/409 |
| 5,180,504 A | 1/1993 | Johnson et al. ............. | 210/767 |
| 5,269,946 A | 12/1993 | Goldhaber et al. ......... | 210/767 |
| 5,270,003 A | 12/1993 | Bernes et al. ................. | 422/44 |
| 5,283,033 A | 2/1994 | Dodrill ........................ | 422/21 |
| 5,372,143 A | 12/1994 | Bernes et al. ............... | 128/762 |
| 5,445,629 A | 8/1995 | Debrauwere et al. ....... | 604/403 |
| 5,451,321 A | 9/1995 | Matkovich ................... | 210/641 |
| 5,472,621 A | * 12/1995 | Matkovish et al. ......... | 210/767 |
| 5,527,472 A | * 6/1996 | Bellotti et al. .............. | 210/767 |
| 5,601,730 A | * 2/1997 | Page et al. ................... | 210/767 |
| 5,695,489 A | 12/1997 | Japuntich .................... | 604/406 |
| 5,702,383 A | 12/1997 | Giesler et al. .............. | 604/409 |
| RE35,804 E | 5/1998 | Stewart ....................... | 210/767 |

\* cited by examiner

*Primary Examiner*—Ivars Cintins
(74) *Attorney, Agent, or Firm*—Daniel D. Ryan; Amy L. H. Rockwell; Michael C. Mayo (57) ABSTRACT

Systems and methods for collecting blood substantially free of residual air and undesired matter also assure that accurate crossmatching and typing of cellular blood components can be done prior to transfusion.

1 Claim, 6 Drawing Sheets

BLOOD COLLECTION METHOD EMPLOYING AN AIR VENTING BLOOD SAMPLE TUBE

FIELD OF THE INVENTION

The invention generally relates to blood collection and processing systems and methods. In a more particular sense, the invention relates to systems and methods for removing white blood cells from red blood cells prior to transfusion or long term storage.

BACKGROUND OF THE INVENTION

Systems composed of multiple, interconnected plastic bags have met widespread use and acceptance in the collection, processing and storage of blood components.

Before storing red blood cells for later transfusion, it is believed to be desirable to minimize the presence of impurities or other materials that may cause undesired side effects in the recipient. For example, because of possible febrile reactions, it is generally considered desirable to store red blood cells with a reduced number of —leukocytes. Filtration is conventionally used to accomplish leuko-reduction.

Systems and methods for reducing the number of leukocytes by filtration in multiple blood bag configurations are described. e.g., in Stewart U.S. Pat. No. 4,997,577, Stewart et al. U.S. Pat. No. 5,128,048, Johnson et al U.S. Pat. No. 5,180,504, and Bellotti et. al. U.S. Pat. No. 5,527,472. In these filtration systems and methods, a transfer assembly dedicated solely to the filtration of leukocytes from red blood cells is used. The transfer assembly also has a second fluid path that bypasses the filtration for the purpose of transferring liquid or venting air around the separation device.

In addition, before transfusing stored cellular blood components like red blood cells, it is important to assure that the blood type of the recipient matches the blood type of the donor. For this reason, conventional blood collection procedures collect several small aliquots or samples of the donated blood component for use in crossmatching and typing the donor's blood prior to transfusion.

Figures 1A, 1B, 1C:
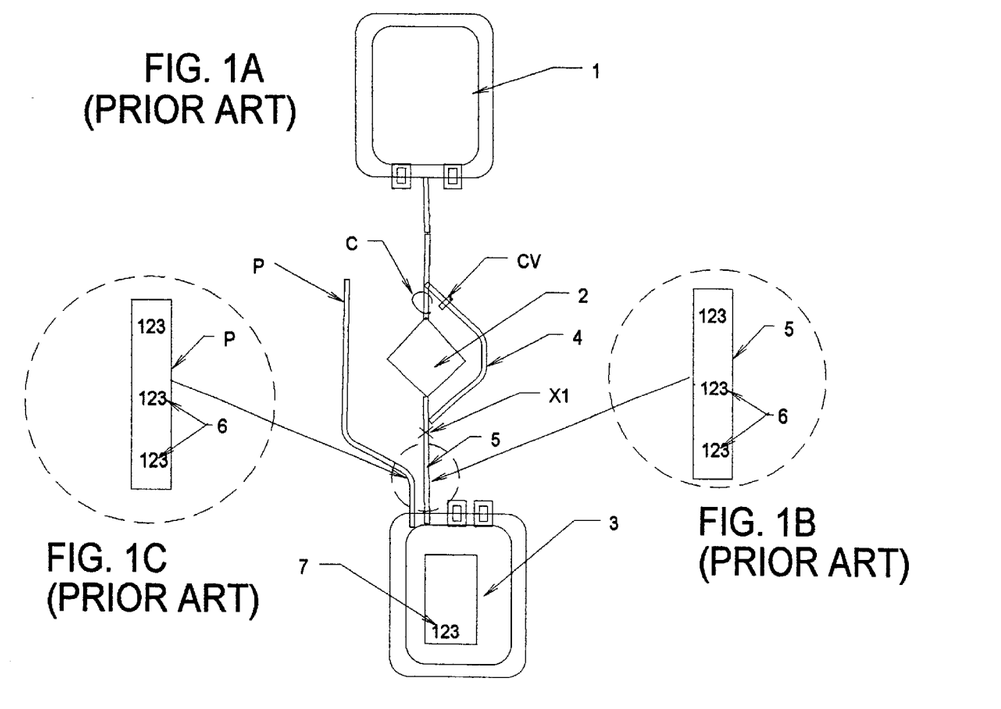
FIG. 1A is a schematic view of a conventional blood collection system to remove leukocytes from red blood cells.
FIGS. 1B and 1C are enlarged views of tubes associated with the system shown in FIG. 1A, which, in use, retain a sample of the processed blood, showing the identification markings used to link the blood samples to the stored blood product following leuko-reduction.
Figure 1D:
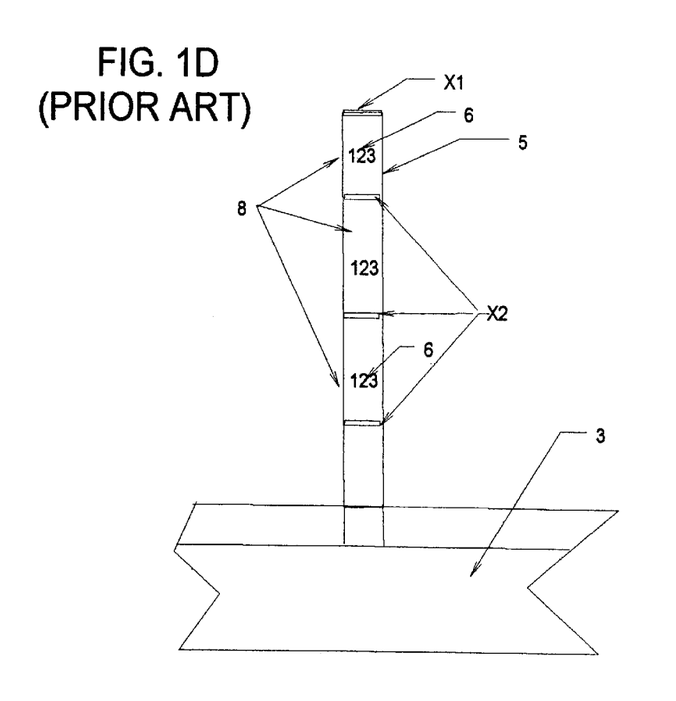
FIG. 1D is an enlarged view of a portion of the prior art system shown in FIG. 1A, showing the tube shown in FIG. 1B after having been segmented by heat sealing into blood sample-retaining pockets.

FIG. 1A shows a representative conventional system that filters leukocytes from red blood cells, vents air from the filtered cells, and creates segmented aliquots of the filtered cells for crossmatching and typing purposes. In use, red blood cells are conveyed from a transfer bag 1 through a leukocyte reduction filter 2 into a storage bag 3. An in-line clamp C controls this flow. Once filtration is completed, the storage bag 3 is squeezed to expel air through a bypass line 4 around the filter 2 into the transfer bag 1. An in-line check valve CV permits one-way fluid flow toward the transfer bag 1, but blocks fluid flow in the opposite direction toward the storage bag 3. A conventional heat sealing device (for example, the Hematron® dielectric sealer sold by Baxter Healthcare Corporation, not shown) forms a hermetic, snap-apart seal X1 in the tubing just downstream of the filter 2. The system components upstream of the seal X1 are disconnected and discarded. As FIG. 1B shows, the remaining tubing 5 (still attached to the storage bag 3) carries alpha or numeric identification markings 6 (which may also be machine-readable), which are printed in a spaced-apart pattern along its length. As FIG. 1A shows, a label 7 on the storage bag 3 carries the same identification markings 6. Using a conventional blood tube stripper (also not shown), the technician displaces residual air from the remaining tubing 5 into the storage bag 3. Upon removal of the tube stripper, the air displaced into the storage bag 3 expels filtered cells into the remaining tubing 5 to occupy the numbered segments 6. As FIG. 1D shows, the sealer is then used to form sealed, snap-apart seals X2 between the identification markings 6, creating segmented pockets 8 where the samples of the filtered cells are retained. The donor-specific label 7 is removed from the transfer bag 1 and attached to the storage bag 3, to thereby preserve a link between the transfer bag 1, the storage bag 3, the numbered blood segments 8, and the donor.

Alternatively, as shown in FIGS. 1A and 1C, the conventional storage bag 3 can also include an a attached tubing segment, or "pigtail" P, which carries the same identification markings 6 printed in a spaced-apart pattern along its length. Once filtration and air venting is completed, the technician uses the blood tube stripper to displace residual air from the pigtail P into the storage bag 3, which in turn displaces filtered cells into the pigtail P. The sealer can then be used to form sealed, snap-apart pockets, as before described, one for each numbered segment, where the samples of the filtered cells are retained.

Prior techniques require the technician to perform multiple, separate functional steps. First, the technician must vent air from the storage bag. Then, the technician must pick up and operate a tube stripper, to expel blood from the storage bag into tubing to create segmented samples for crossmatching and blood typing.

SUMMARY OF THE INVENTION

The invention provides more straightforward and convenient systems and methods to remove undesired matter from blood cells, which permit air venting and sample expulsion to take place in one functional step. The invention obviates the need for tube strippers, thereby simplifying the overall blood manipulation process. Still, the invention assures that accurate crossmatching and typing of the blood occurs.

One aspect of the invention provides a blood processing assembly comprising a blood receiving container having first and second ports. A first flow path is included, which has an inlet region for coupling the first flow path in fluid communication with a blood source container and an outlet region coupled to the first port. The first flow path includes a separation device positioned between the inlet and outlet regions that separates undesired matter from blood en route the blood receiving container. A second flow path is also included, which has an entry region coupled to the second port, and not the first port, and an exit region coupled to the inlet region of the first flow path at a junction. The second flow path includes a one-way valve between the entry region and the exit region. The one-way valve permits fluid flow through the second flow path, bypassing the separation device, only from the blood receiving container toward the blood source container and not vice versa.

Another aspect of the invention provides a method of using the assembly. The method directs blood through the first flow path and separation device to remove undesired matter. The blood is collected in the blood receiving container after passage through the separation device. The method squeezes the blood receiving container to expel residual air from the blood receiving container through the second flow path. The one-way valve permits air flow only in a direction away from the blood receiving container, and not vice versa. The method squeezes the blood receiving container to convey a sample of blood from the collection container into the second flow path. Again, the one-way valve permits blood flow only in the direction away from the blood receiving container, and not vice versa. The method seals the second flow path to retain the sample of blood in the second flow path.

By virtue of the above described structure and method of use, a sample of blood from the blood receiving container can be transferred into the second flow path simply by squeezing the blood receiving container, and coincident with air venting. There is no need for separate air venting and blood sample collecting steps, and there is no need for a tube stripper.

In a preferred embodiment, the separation device removes leukocytes from blood.

Other features and advantages of the invention will become apparent upon review of the following description, drawings, and appended claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 2:
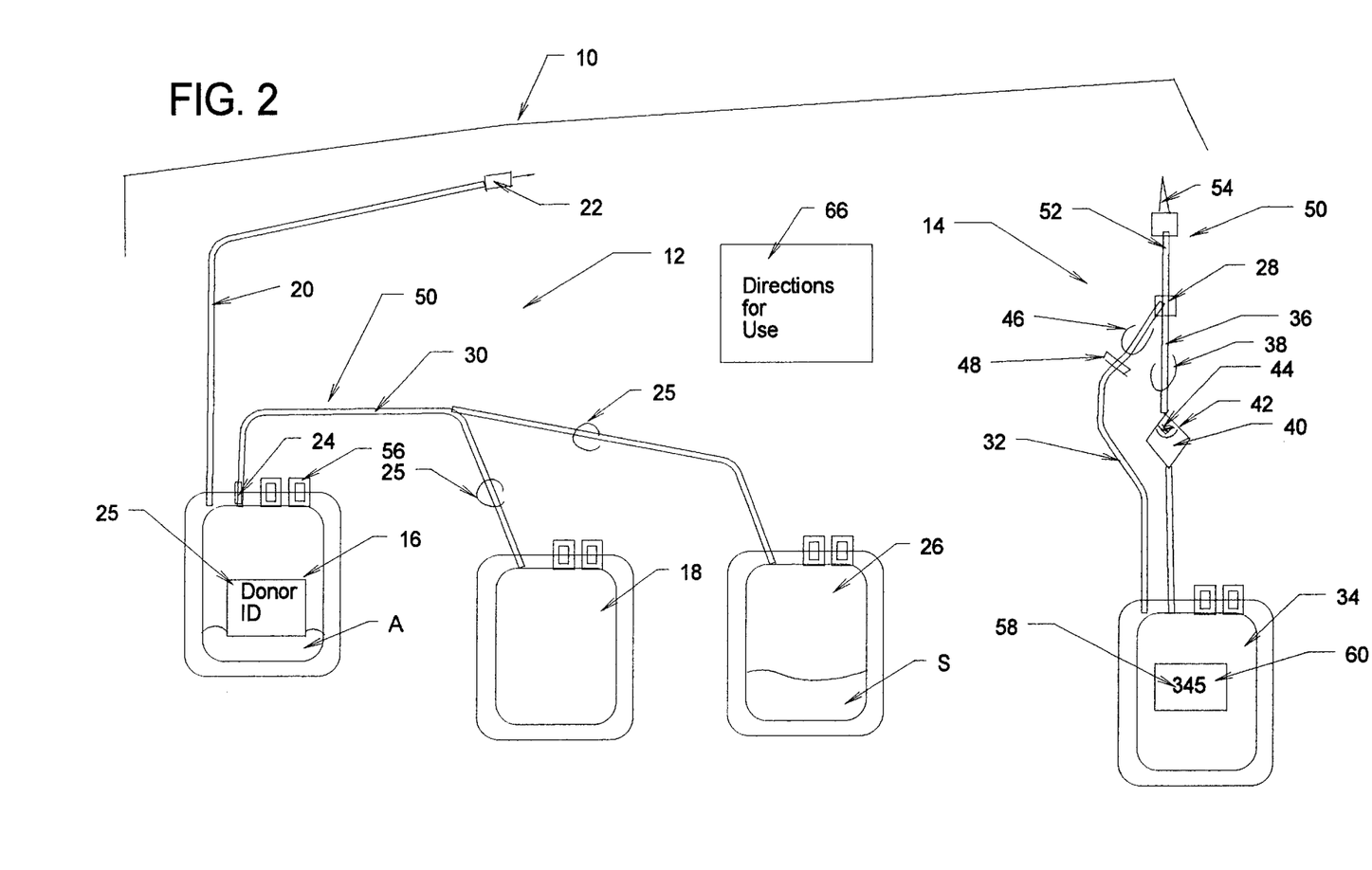
FIG. 2 is a schematic view of a blood collection system having a blood collection assembly and a blood filtration assembly, which embodies features of the invention.

A blood collection system 10, which embodies features of the invention, is shown in FIG. 2. The system 10 comprises a blood collection and processing assembly 12 and a filtration assembly 14.

The blood collection and processing assembly 12 comprises a multiple blood bag system having a primary bag or container 16 and one or more integrally attached transfer bags or containers 18 and 26. In use, the primary bag 16 (which is typically also called a donor bag) receives whole blood from a donor through integrally attached donor tubing 20 by means of a phlebotomy needle 22. A suitable anticoagulant A (e.g., CPD or ACD) is contained in the primary bag 16.

The transfer bag 18 is attached to the primary bag 16 by integrally attached transfer tubing 30. The transfer bag 18 is intended to receive the platelet-rich plasma blood component for processing. The transfer bag 26 contains a suitable storage solution S for red blood cells. The storage solution S will ultimately be conveyed from the transfer bag 26 to the primary bag 16 during the course of blood processing. A representative storage solution S is disclosed in Grode et al U.S. Pat. 4,267,269. A conventional in-line frangible cannula 24 and in-line clamps 25 control fluid flow through the tubing 30. 18 among the bags 16, 18, and 26.

All of the bags 16, 18, and 26 and tubing 30 associated with the processing assembly 12 can be made from conventional approved medical grade plastic materials, such as polyvinyl chloride plasticized with di-2-ethylhexylphthalate (DEHP). The blood collection assembly 12, once sterilized, constitutes a sterile, "closed" system, as judged by the applicable standards in the United States.

Preferably (as FIG. 2 shows), before whole blood is collected, a removable donor-specific label 25 is attached to the primary blood bag 16. The label 25 carries a unique identification number assigned to the particular donor at the time of donation.

Whole blood is collected from the donor in the primary bag 16. The whole blood is separated by centrifugation in the primary bag 16 into red blood cells and platelet-rich plasma. In the process of centrifugally separating these components, a layer rich in leukocytes forms between the red blood cells and the platelet-rich plasma.

Figure 3:
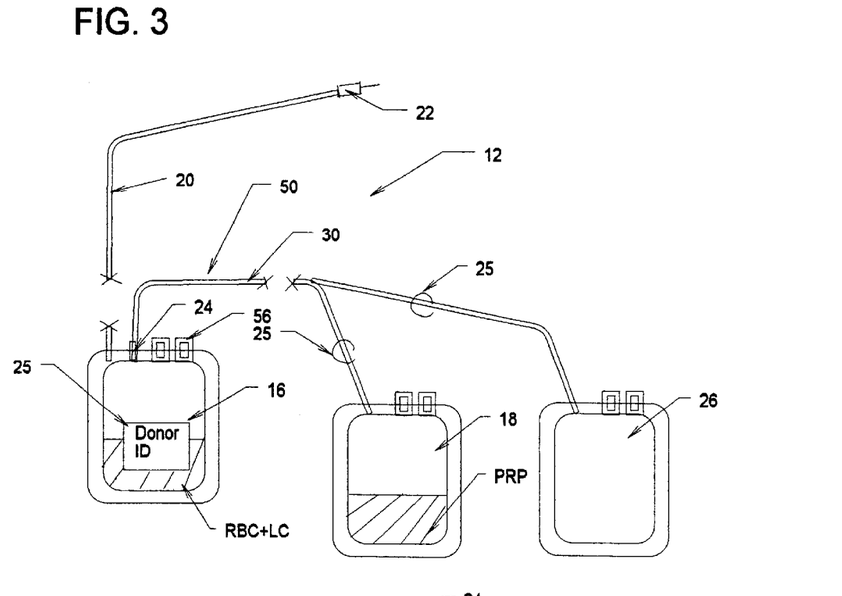
FIG. 3 is a schematic view of the blood collection assembly shown in FIG. 2, after whole blood collected in the assembly has been centrifugally processed into red blood cells containing leukocytes, retained in a primary bag, and platelet-rich plasma, retained in a transfer bag.

The platelet-rich plasma is transferred by conventional techniques into the transfer bag 18, leaving the red blood cells (designated RBC) and leukocytes (designated LC) in the primary bag 16. The red cell storage solution S is then transferred from the bag 26 to the primary bag 16 through the transfer tubing 30. As FIG. 3 shows, the donor tubing 20 and the bags 18 and 26 are detached using snap apart seals "x" formed by a conventional dielectric sealing device, as previously described.

The platelet-rich plasma can undergo subsequent centrifugal separation within the first transfer bag 18 into platelet concentrate and platelet-poor plasma. An additional preattached transfer bag (not shown) can be included to receive the platelet-poor plasma.

As FIG. 2 shows, the filtration assembly 14 comprises an initially separate subassembly not joined to the blood processing assembly 12. The entire filtration assembly 14 can be provided in a "dry" condition, free of any fluids, storage mediums, and the like (except for any entrapped air).

The filtration assembly 14 includes a storage bag 34 and an associated main tube path 36. The tube path 36 further includes an inline device 40 for separating undesired matter from blood cells.

The filtration assembly 14 also includes an integrally attached tube segment 32. The far end of the tube segment 32 joins the main tube path 36 upstream of the separation device 40, via a conventional Y-coupler 28.

The storage bag 34, main tube path 36, and the tube segment 32 can all made of low cost medical grade plastic materials, such as polyvinyl chloride plasticized with DEHP.

In the illustrated embodiment, the filtration assembly 14 serves to remove undesired matter from blood cells by filtration. For this reason, the assembly 14 and the device 40 will be referred to as a "filtration" assembly and device. It should be appreciated, however, that separation can occur by various centrifugal and non-centrifugal techniques, and not merely "filtration" in the A technical sense. Separation can occur by absorption, columns, chemical, electrical, and electromagnetic means. The term "filtration assembly" or "filtration device" is broadly used in this specification encompass all of these separation techniques as well.

It should be appreciated that the filtration assembly 14 can be used to remove all types of undesired materials from different types of blood cells, depending upon its particular construction. In the illustrated embodiment, the filtration assembly 14 is intended to remove leukocytes from the red blood cells prior to storage. Still, it should be appreciated the features of the assembly 14 and its method of use can be used for separating matter from other blood products, such as plasma or platelets or whole blood itself.

In this arrangement, the filtration device 40 includes a housing 42 containing a conventional filtration medium 44 suited for the removal of leukocytes from red blood cells. The filtration medium 44 can include cotton, wool, cellulose acetate or another synthetic fiber like polyester.

A clamp 38, e.g., a conventional roller clamp, regulates flow through the main tube path 36 into the storage bag 34 via the filtration device 40.

A one-way check valve 48 controls fluid flow through the tube segment 32. The valve 48 does not allow passage of fluid (liquid or air) in the direction of the storage bag 34. However, the valve 48 does allow passage of fluid (liquid and air) in the opposite direction, away from the storage bag 34.

If desired, another conventional clamp 46 can be provided to further regulate flow through the tube segment 32 upstream of the valve 48.

Figure 4:
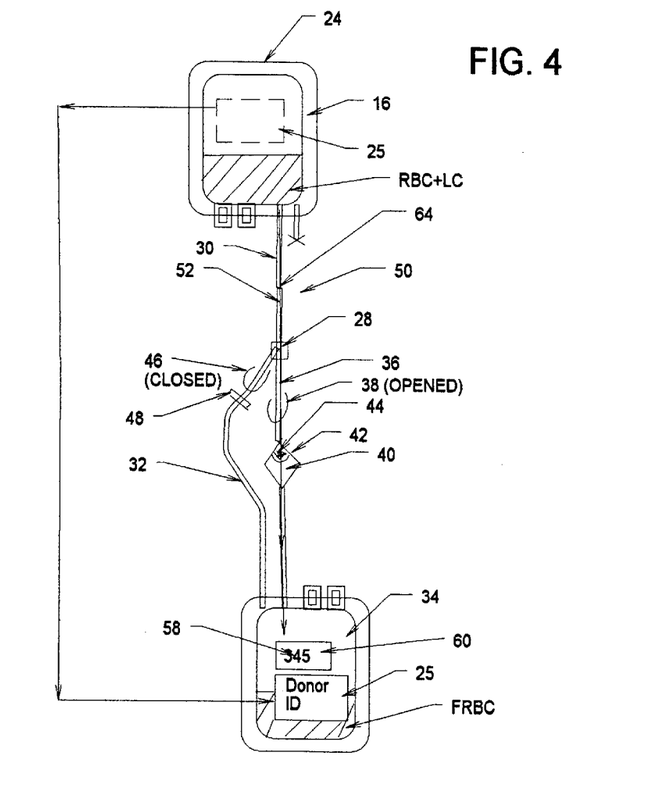
FIG. 4 is a schematic view showing the connection of the blood filtration assembly to the primary bag of the blood collection assembly for the purpose of removing leukocytes from the red blood cells while being conveyed to a storage bag.

A connection assembly 50 is associated with the initially separate blood collection and filtration assemblies 12 and 14. The connection assembly 50 permits selective attachment of the filtration assembly 14 to the blood collection assembly 12, as FIG. 4 shows. The technician closes both clamps 38 and 46 before attachment of the assemblies 12 and 14.

In the illustrated and preferred embodiment, both assemblies 12 and 14, once sterilized, comprise sterile, "closed" systems, as judged by the applicable United States standards. In this arrangement, the connection assembly 50 serves to attach the donor bag 16 to the filtration assembly 14 in a manner that preserves the sterile integrity of the closed systems 12 and 14.

The connection assembly 50 can be variously constructed. It can comprise the conventional sterile connecting system disclosed in Spencer U.S. Pat. No. 4,412,835 (not shown), which is incorporated herein by reference. In this arrangement (which is shown in FIG. 4), the system forms a molten seal between the transfer tube 30 of the primary bag 16 (after having been separated from the transfer bags 18 and 26, as FIG. 3 shows) with the end 52 of the tube path 36 of the filtration assembly 14. Once cooled, a sterile weld 64 is formed. In an alternate arrangement (not shown), the connection assembly 48 can comprises two mating sterile connection devices of the type shown in Granzow et al U.S. Pat. Nos. 4,157,723 and 4,265,280, which are incorporated herein by reference. In either case, the attachment is made without otherwise opening the assemblies 12 and 14 to communication with the atmosphere. As a result, the filtered cells can be stored for the maximum allowable dating period.

The end 52 of the tube path 36 can also carry a conventional blood spike 54. Instead of forming a sterile weld 64, the technician can insert the blood spike 54 in conventional fashion into a port 56 of the primary bag 16, thereby joining the two assemblies 12 and 14 together. This attachment technique, however, opens the assemblies 12 and 14 to communication to the atmosphere. As a result, the filtered cells must be transfused within 24 hours.

Once attachment of the assemblies 12 and 14 is made, the donor bag 16 is gently squeezed to mix the unfiltered red blood cells. The donor bag 16 is lifted above the storage bag 34 (as FIG. 4 shows), and the flow clamp 38 is opened. The red blood cells (designated RBC) are conveyed by gravity flow from the donor bag 16 through the tube path 36 and filtration device 40 and into the transfer bag 34. The closed clamp 46 or the check valve 48 (in the absence of or the opening of the clamp 46) prevents flow through the tube segment 32.

In the process, the leukocytes are removed by the filtration device 40 from the blood cells. Once the red blood cells are transferred, the donor specific label 25 is removed from the primary bag 16 and applied to the storage bag 34, to preserve the link to the donor.

Figures 5, 6A, 6B:
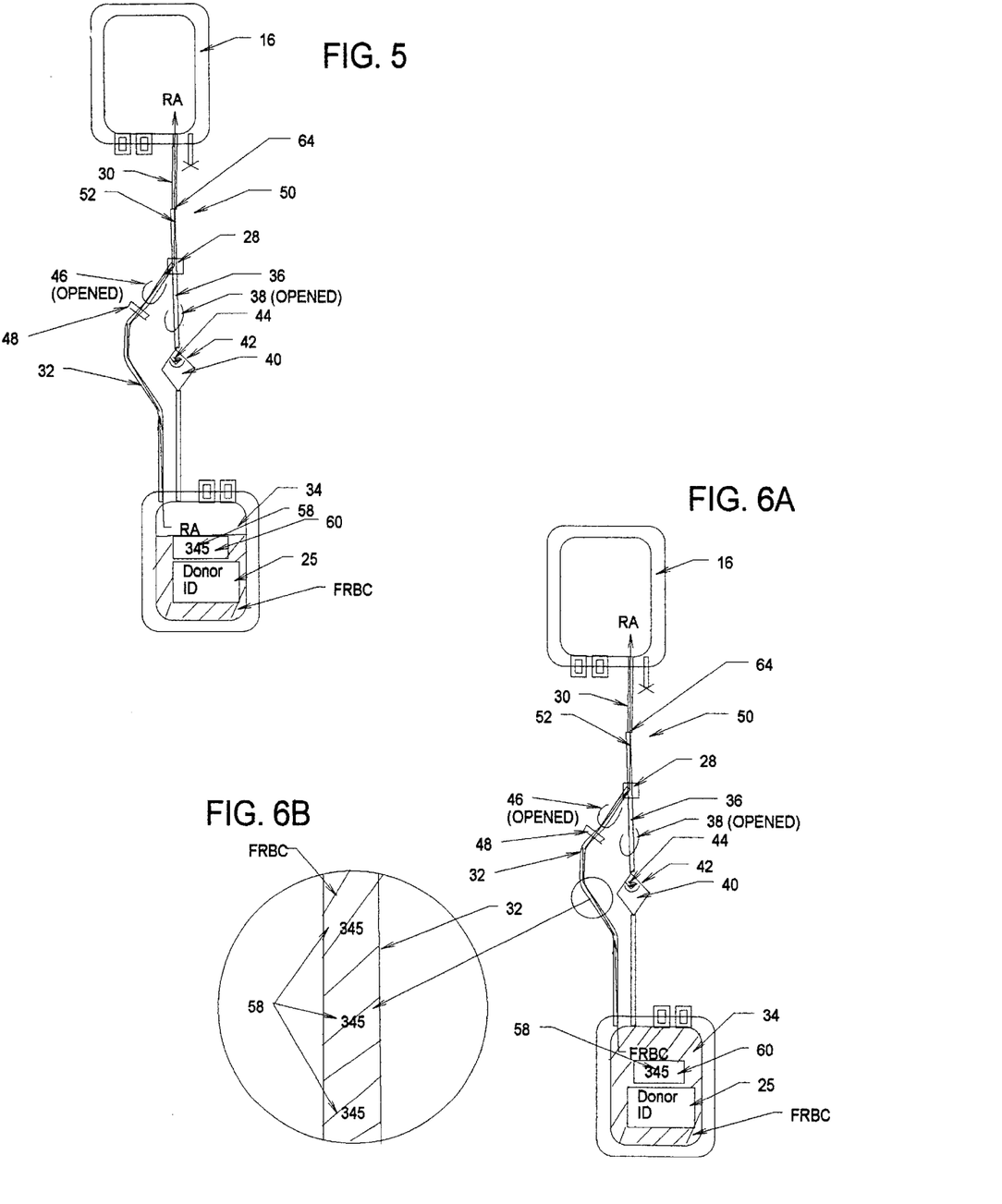
FIG. 5 is a schematic view of the connected blood filtration assembly and the blood collection assembly after the red blood cells have been filtered, showing the venting of residual air from the storage bag into the primary bag through a tube segment that bypasses the filter.
FIG. 6A is a schematic view of the connected blood filtration assembly and the blood collection assembly after residual air has been vented from the storage bag, showing the advancement of filtered red blood cells into the same tube segment used to vent air from the storage bag without the use of a tube stripper.
FIG. 6B is an enlarged schematic view of the tube segment shown in FIG. 6A, into which filtered red blood cells have been advanced while venting air from the storage bag, showing the identification markings printed on the tube segment.

As FIG. 5 shows, once the filtration is completed, the clamp 46 is opened. The storage bag 34 is squeezed gently. The squeezing expels residual air (designated RA in FIG. 5) from the storage bag 34 through the tube segment 32 and into the primary bag 16. The tube segment 32 thereby provides an air venting path around the filtration device 40. The check valve 48 prevents back flow of air and other fluid toward the storage bag 34.

As FIGS. 6A and 6B show, as residual air RA is removed from the storage bag 34, the same squeezing action will displace filtered red blood cells (designated FRBC) from the storage bag 34 into the tube segment 32. The filtered red blood cells FRBC from the bag 34 fill the tube segment 32. The check valve 48 prevents back flow of filtered red blood cells FRBC toward the storage bag, retaining the samples in the tube segment 32.

As FIG. 6B shows, the tube segment 32 carries alpha or numeric identification markings 58 printed in a spaced-apart series along its length. The markings 58 can also be formatted to be machine readable. A label 60 on the storage bag 34 also carries the same identification marking 58, which can also be formatted to be machine readable.

Figures 7A, 7B:
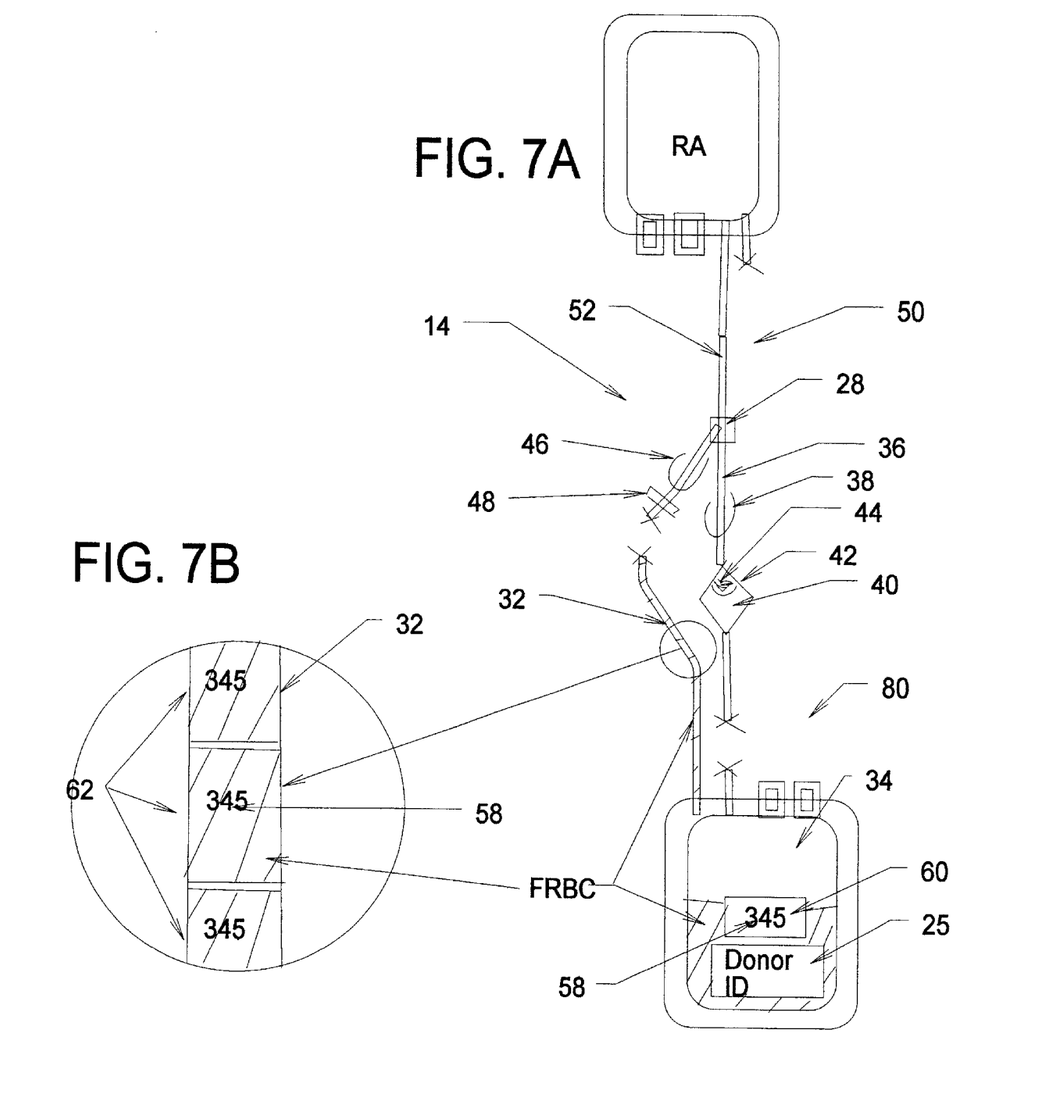
FIG. 7A is a schematic view of the storage bag and attached tube segment, after having been separated from the rest of the system for storage of the red blood cells.
FIG. 7B is an enlarged schematic view of the tube segment attached to the storage bag shown in FIG. 7A, showing the tube segment after having been segmented by heat sealing into blood sample-retaining pockets.

As FIG. 7A shows, when the desired volume of filtered cells occupies the marked tube segment 32, the technician employs the dielectric tube sealer previously described to form snap-apart seals "x" in the tube path 36 downstream of the filter 40, as well as in the marked tube segment 32 above the uppermost segment marking 58, which is preferably located near and downstream of the check valve 48. This frees the filter 40, associated dependent upstream tube path 36 and tube segment 32, and the attached primary bag 16, which is now empty, except for the residual air RA. These detached components are discarded as a unit.

As FIG. 7B shows, the technician uses the dielectric sealer to form sealed, snap-apart pockets 62 along the length of the tube segment 32, which is still attached to the storage bag 34. The pockets 62 retain discrete samples of the filtered cells. The tube segment 32 thereby serves, not only as an air venting path around the filtration device 40, but also as a segmented blood sample tube attached to the storage bag 34. Unlike prior segmented sample tubes, the tube segment 32 can be filled with blood samples by squeezing the storage bag 34, and without need of a conventional tube stripping device.

The resulting fully processed assembly 80 (shown in FIG. 7A) comprises the air-vented storage bag 34, to which the tube segment 32 with sealed pockets 62 retaining the samples of the donor's filtered blood is secured. The storage bag 34 also carries the donor-specific label 25 and linking sample label 60.

The red blood cells, now substantially reduced of leukocytes, are stored in the air-vented storage bag 34. The attached sample pockets 62 of the filtered blood can be separated from the tube segment 32 when desired, and can be analyzed at a convenient time prior to transfusion for crossmatching and typing purposes.

The invention assures direct traceability between a leukocyte-reduced blood product for transfusion and the donor from whom the blood is obtained.

In the illustrated embodiment (see FIG. 2), the system 10 includes directions 66 for using the system 10 in the manner above described.

The foregoing embodiment shows the features of the invention in the context of a filtration assembly 14, which is, during use, coupled to a processing assembly 12 to filter leukocytes from red blood cells. The invention, of course, can be used in the processing of other kinds of blood components and in association with other blood collection system configurations.

Figure 8:
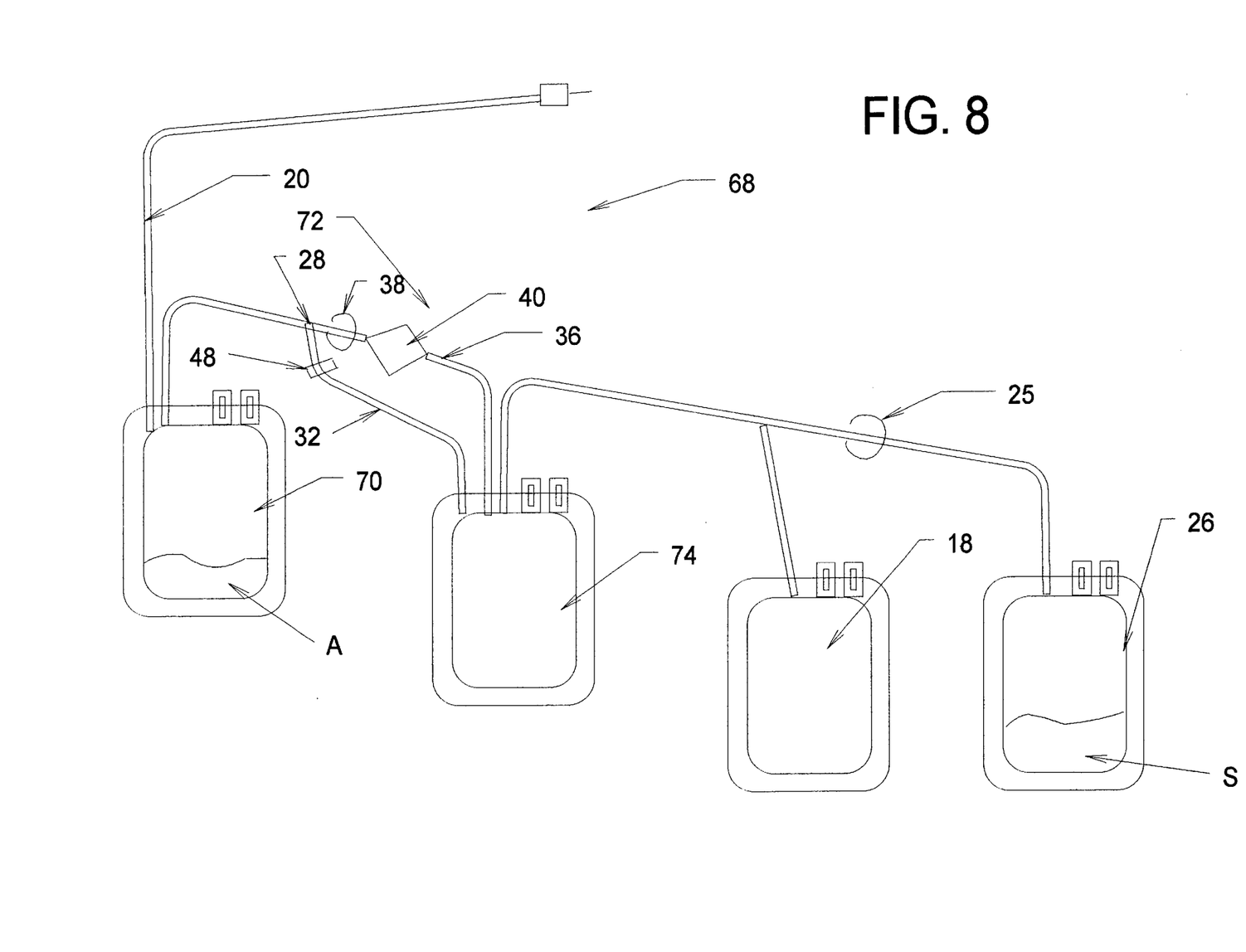
FIG. 8 shows a schematic view of another blood collection system having an integrally attached a blood filtration assembly, which embodies features of the invention.

For example, as FIG. 8 shows, an integral blood processing system 68 can include a whole blood collection bag 70 (containing an anticoagulant A) to which a filtration assembly 72 embodying the features of the invention is integrally attached. The assembly 72 includes a transfer bag 74 to which the main tube path 36, the in line filter device 40, and tube segment 32 are coupled in the same manner shown in FIG. 2. The tube segment 32 also includes the one-way valve 48, as also previously described. Additional transfer bags 18 and 26 are integrally attached to the transfer bag 74, in the same manner the bags 18 and 26 are integrally attached to the primary bag 16 in FIG. 2. Like the primary bag 16 shown in FIG. 2, the whole blood collection bag 70 in FIG. 8 includes a donor tube 20.

In use, a unit of whole blood is collected in the bag 70, where it is mixed with anticoagulant A. After the donor tube 20 is disconnected, whole blood is transferred from the bag 70 through the tube path 36 and filter device 40, into the transfer bag 74. In this arrangement, the filter device 40 removes leukocytes from whole blood. In the same manner described in connection with the assembly 14, the transfer bag 74 is squeezed to vent residual air through the tube segment 32 into the collection bag 70. Squeezing of the transfer bag 74 conveys a sample of the filtered whole blood into the tube segment 32. The tube segment 32 and tube path 36 are sealed, and the collection bag 70 is disconnected. Sample segments are formed along the tube 36 still attached to the transfer bag 74, in the manner already described. This leaves the transfer bag 74, sample tube segment 32, and transfer bags 18 and 26 remaining as an integrated assembly.

The filtered whole blood is thereafter centrifugally separated in the transfer bag 74 into red blood cells and platelet-rich plasma. The platelet-rich plasma is expressed into the transfer bag 18 for storage or further processing. The solution S is added to the red blood cells remaining in the transfer bag 74, which becomes the storage container for the red blood cells. The blood samples of the filtered whole blood can be separated from the tube segment 32 when desired, and can be analyzed at a convenient time prior to transfusion for crossmatching and typing purposes.

Various features of the invention are set forth in the following claims.

We claim:

1. A method for processing blood comprising the steps of
providing a blood processing assembly including a blood receiving container having first and second ports; a first conduit including an inlet for coupling the first conduit in fluid communication with a blood source container and an outlet coupled to the first port; a separation device positioned between the inlet and outlet of the first conduit that separates undesired matter from blood en route the blood receiving container; and a second conduit including an entry coupled to the second port and not the first port and an exit coupled to the first conduit at a junction between the separation device and the inlet of the first conduit, the second conduit including a one-way valve between the entry and the exit of the second conduit that permits fluid flow through the second conduit, bypassing the separation device, only from the blood receiving container toward the blood source container and not vice versa,
directing blood from the blood source container through only the first conduit and into the separation device to remove undesired matter,
directing blood from the separation device into the blood receiving container only through the first port, whereby the second conduit remains free of contamination with residual blood,
subjecting the blood receiving container to a single squeezing action that, as the squeezing action commences, first expels residual air from the blood receiving container only through the second port and only through the second conduit into the blood source container, bypassing the separation device and, as the squeezing action continues, conveys a sample of blood from the blood receiving container only into the second conduit without using a blood tube stripper, the one-way valve, as squeezing action commences, permitting air flow only in the direction away from the blood receiving container and not vice versa and, as the squeezing action continues, preventing backflow of the blood sample toward the blood receiving container, and
sealing the second conduit to seal the sample of blood retained in the second conduit, whereby the sample collected during the single squeezing action is free of air and uncontaminated with residual blood.

* * * * *